US010245151B2

(12) United States Patent
Davignon et al.

(10) Patent No.: US 10,245,151 B2
(45) Date of Patent: *Apr. 2, 2019

(54) STEPPED TIBIAL BASEPLATE

(71) Applicant: Stryker Corporation, Kalamazoo, MI (US)

(72) Inventors: Robert Davignon, Morris Plains, NJ (US); Michael C. Ferko, Warwick, NY (US); Stuart L. Axelson, Jr., Succasunna, NJ (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,884

(22) Filed: Jun. 10, 2016

(65) Prior Publication Data

US 2016/0278930 A1    Sep. 29, 2016

Related U.S. Application Data

(63) Continuation of application No. 14/292,217, filed on May 30, 2014, now Pat. No. 9,387,085.

(51) Int. Cl.
*A61F 2/38* (2006.01)

(52) U.S. Cl.
CPC ...... *A61F 2/389* (2013.01); *A61F 2002/3895* (2013.01); *Y10T 29/49002* (2015.01)

(58) Field of Classification Search
CPC ...... A61F 2/384; A61F 2/3863; A61F 2/3868; A61F 2/389; A61F 2/38; A61F 2/3886
See application file for complete search history.

(56) References Cited

U.S. PATENT DOCUMENTS

| | | | |
|---|---|---|---|
| 6,190,415 B1 | 2/2001 | Cooke et al. | |
| 6,235,060 B1 * | 5/2001 | Kubein-Meesenburg | ............... A61F 2/38 623/18.11 |
| 8,906,064 B2 * | 12/2014 | Timm | ............ A61B 17/7068 606/248 |
| 9,005,299 B2 * | 4/2015 | Muratoglu | ............ A61F 2/3886 623/20.28 |
| 9,387,085 B2 * | 7/2016 | Davignon | ............ A61F 2/389 |

(Continued)

FOREIGN PATENT DOCUMENTS

WO    2012162180 A1    11/2012

OTHER PUBLICATIONS

Extended European Search Report for Application No. 15169873.5 dated Aug. 25, 2015.

*Primary Examiner* — Alvin Stewart
(74) *Attorney, Agent, or Firm* — Lerner, David, Littenberg, Krumholz & Mentlik, LLP

(57) ABSTRACT

Disclosed herein are orthopedic implants having a medial portion and a lateral portion, each of the medial and lateral portions having a proximal surface and a distal surface opposite the proximal surface. An intermediate portion joins the medial and lateral portions, wherein the intermediate portion has a proximal surface angled to the proximal surfaces of the medial and lateral portions about a longitudinal axis of the orthopedic implant. The proximal surface of the medial portion is stepped from the proximal surface of the lateral portion about the longitudinal axis. The proximal surfaces of the medial and lateral portions are configured to receive corresponding medial and lateral inserts.

18 Claims, 13 Drawing Sheets

(56) References Cited

U.S. PATENT DOCUMENTS

| | | | |
|---|---|---|---|
| 9,707,085 B2* | 7/2017 | Muratoglu | A61F 2/3886 |
| 2001/0047211 A1 | 11/2001 | Leclercq et al. | |
| 2004/0138755 A1* | 7/2004 | O'Connor | A61F 2/3868 |
| | | | 623/20.32 |
| 2006/0195195 A1* | 8/2006 | Burstein | A61F 2/3868 |
| | | | 623/20.33 |
| 2006/0212124 A1* | 9/2006 | Siebel | A61F 2/389 |
| | | | 623/20.31 |
| 2007/0100463 A1 | 5/2007 | Aram et al. | |
| 2012/0035735 A1 | 2/2012 | Sanford et al. | |
| 2012/0179266 A1 | 7/2012 | Collazo | |
| 2012/0310361 A1* | 12/2012 | Zubok | A61F 2/30734 |
| | | | 623/20.32 |
| 2012/0310362 A1* | 12/2012 | Li | A61F 2/38 |
| | | | 623/20.32 |
| 2013/0131819 A1* | 5/2013 | Parisi | A61F 2/3886 |
| | | | 623/20.33 |
| 2013/0131820 A1 | 5/2013 | Wentorf et al. | |
| 2013/0245777 A1 | 9/2013 | Jerry | |
| 2014/0039636 A1 | 2/2014 | Kurtz | |
| 2014/0163687 A1* | 6/2014 | Parisi | A61F 2/3886 |
| | | | 623/20.33 |

\* cited by examiner

STEPPED TIBIAL BASEPLATE

CROSS-REFERENCE TO RELATED APPLICATIONS

This application is a continuation of U.S. application Ser. No. 14/292,217, filed on May 30, 2014, the disclosure of which is incorporated herein by reference.

FIELD OF THE INVENTION

The present invention relates to implants adapted for placement on stepped resected surfaces of a proximal tibia and in particular relates to such implants when placed on that stepped resected surfaces that have a lateral portion located superiorly to a medial portion thereof about a mechanical axis of the proximal tibia.

BACKGROUND OF THE INVENTION

In joint arthroplasty procedures, positioning of prosthetic implant or components is one mechanism used in restoring joint functionality. For instance, in knee arthroplasty procedures, positioning of femoral, tibial and/or patellar components is generally necessary in restoring natural mechanical alignment between the distal femur and proximal tibia, for example. Natural mechanical alignment is generally defined as the angle between the femoral and tibial mechanical axes.

Patients typically have some deviation between the femoral and the tibial mechanical axes, resulting in a natural varus or valgus orientation of the knee joint. This deviation generally increases due to natural degeneration and wear or may increase due to injury. Therefore, it is often a goal of knee arthroplasty procedures, for example, to restore the patient's natural varus/valgus orientation.

Two common approaches to orthopaedic implant placement in knee arthroplasty procedures are classical mechanical alignment and anatomic alignment. In classical mechanical alignment, the tibia is generally resected perpendicular to the patient's tibial mechanical axis. Aligning a tibial implant perpendicular to the tibial mechanical axis will generally load each condyle equally and will align joint forces in a compressive orientation down the axis of the tibia. This loading is beneficial due to the orthotropic nature of bone that causes it to be strongest in axial loading such that joint forces are spread out equally on both the medial and lateral condyles. The patient's natural deviation from mechanical alignment is typically compensated by making an ideally equal and opposite cut on the femur in flexion and extension. This may lead, however, to removing more bone than is desirable. With an anatomic approach, tibial cuts are oriented at a slope towards the patient's natural varus/valgus alignment. This approach may better recreate the patient's natural kinematics and conserve bone by avoiding compensatory cuts. However, one problem that has been recognized is that such an approach may also lead to tibial baseplate loading that is off axial, providing a mechanical disadvantage at the bone/device interface by introducing shear loads, for example.

In one analysis of 544 patient tibiae, it was shown that tibiae have on average a 2.76 degree of natural tibial varus and thus have a lateral condyle that is located superiorly to the medial condyle relative to the tibial mechanical axis. Literature sources have shown that healthy patients tend to have a similar degree of joint and tibial varus. Publications have also shown more extreme joint deviations from mechanical in osteoporotic patients, which on average tend to be in tibial varus. Noting these findings, it would indicate that mechanical surgical preparation on the tibia would tend to resect relatively more bone on the lateral tibia, and require an equivalent over resection on the medial femur. It would also indicate that anatomic alignment would, on average, place implants in 2-3 degrees tibial varus resulting in off axis loading.

BRIEF SUMMARY OF THE INVENTION

Accordingly, tibial baseplates of the present invention have medial and lateral portions corresponding to differing resection depths in the medial and lateral tibial condyles. The differing resection depths form "stepped surfaces" that allow a tibial baseplate, once implanted, to retain anatomic orientation while conserving bone in the proximal tibia. The resection depths each form a cut plane that is preferably perpendicular to the tibial mechanical axis in a frontal view.

Current monolithic tibial implants are generally planar in a coronal view and do not allow for implant placement on stepped resected surfaces. The tibial baseplates of the present invention take into consideration the natural tibia varus present in a majority of tibiae. Such a monolithic tibial baseplate is manufactured with an average step built in between the medial and lateral condyles with the lateral plateau being slightly superior to the medial plateau about a longitudinal axis of the baseplate.

In some embodiments, acceptable limits for offsetting tibial baseplate placement from mechanical are determined and the step is placed within such acceptable limits to maximize the patient population captured by the design. The stepped resection height in one embodiment, conserves more bone and captures a larger percentage of patients in anatomic positioning while requiring less offset from mechanical alignment. In addition to conserving bone and allowing implant placement to be closer to tibial mechanical alignment, the anterior medial tibial eminence tends to be higher than the anterior lateral eminence. Noting this, the anterior-medial tibia is preferably thicker on the medial side by remaining at the bone height superiorly across the eminence. This increases the component physical strength and reduces chance of fracture in required FDA component strength testing, while minimizing uncapped bone.

In addition to the implant having offset heights from one compartment to another, tibial baseplates of the present invention are designed and manufactured to incorporate offset internal and external rotations from one tibial compartment to the other, offset and/or differential posterior slopes, along with anterior and posterior positioning seen between medial and lateral implant condyles, thus allowing for a more anatomic and bone conserving baseplate.

In accordance with one embodiment, a tibial baseplate comprises a medial portion having a first proximal surface and a first distal surface opposite the first proximal surface, the first proximal surface being configured to receive a medial insert, a lateral portion having a second proximal surface and a second distal surface opposite the second proximal surface, the second proximal surface being configured to receive a lateral insert, and an intermediate portion joining the medial and lateral portions, wherein the intermediate portion has a proximal surface angled to the proximal surfaces of the medial and lateral portions about a longitudinal axis of the tibial baseplate, such that the proximal surface of the medial portion is stepped from the proximal surface of the lateral portion about the longitudinal axis.

In accordance with a further embodiment, a tibial baseplate may comprise one engagement feature extending distally from one of the medial, proximal, or intermediate portions. The engagement feature may be, for example, a peg or a keel. In a still further embodiment, the proximal surface of the intermediate portion may be based on patient data.

In accordance with a further embodiment, the proximal surface of the intermediate portion may be angled between 2 and 4 degrees to the longitudinal axis of the tibial baseplate. In at least one embodiment, the proximal surfaces of the medial and lateral portions may lie along planes that are parallel and offset to one another. In one embodiment, the distal surfaces of the medial and lateral portions are coplanar.

In a still further embodiment, the baseplate comprises a first transition region between the medial portion and the intermediate portion and a second transition region between the intermediate portion and the lateral portion, wherein the first transition region forms a first radius and the second transition region forms a second radius.

In accordance with a further embodiment, a method of designing a tibial baseplate comprises the steps of determining a vertical offset between resected surfaces of a medial and a lateral tibial condyle, and providing a tibial baseplate having a medial portion and a lateral portion, the medial and lateral portions having distal surfaces being vertically offset from one another, wherein the vertical offset between the medial and lateral portions is substantially equal to the determined vertical offset between the resected surfaces of the medial and lateral tibial condyles.

According to one embodiment, the step of determining the vertical offset between the resected surfaces of the medial and lateral tibial condyles comprises the steps of obtaining patient data of a varus/valgus angle of at least one knee joint. In a further embodiment, the patient data comprises a database of patient data.

In a still further embodiment, a fixation feature is provided extending distally from at least one of the medial or lateral portions of the tibial baseplate. The engagement feature may, for instance, be a peg or a keel.

In accordance with another embodiment, a stepped tibial baseplate is a modular tibial baseplate. For instance, in this embodiment, the medial and lateral baseplate portions may be separate implant components that are not connected to one another. In these designs, the low points or sulcus of the medial and lateral compartments may represent an initial position of the medial and lateral baseplate portions. The baseplate portions may be adjusted accordingly to optimal internal-external rotation, flexion-extension axis, and cortical tibial rim coverage conditions. The baseplate portions may then be adjusted from their natural varus alignment to perpendicular conditions relative to a longitudinal axis of a patient's bone, for instance the functional mechanical axis of a tibia.

In accordance with another embodiment, a stepped tibial baseplate is a monolithic stepped tibial baseplate having connected medial and lateral portions. For such monolithic implants, the stepped tibial baseplate is designed with fixed varus, such that there is a fixed height difference between the medial sulcus and lateral sulcus. Stepped resection planes may be made perpendicular to a longitudinal axis of the bone, for instance the tibial mechanical axis. Further, the medial compartment sulcus of the implants may be synchronized with a natural medial sulcus of a patient. Finally, in order to make varus/valgus adjustments of a couple degrees, the monolithic baseplate may rotated on the medial sulcus point in the coronal plane, for example, until the lateral sulcus of the baseplate is even with natural lateral sulcus of the patient.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
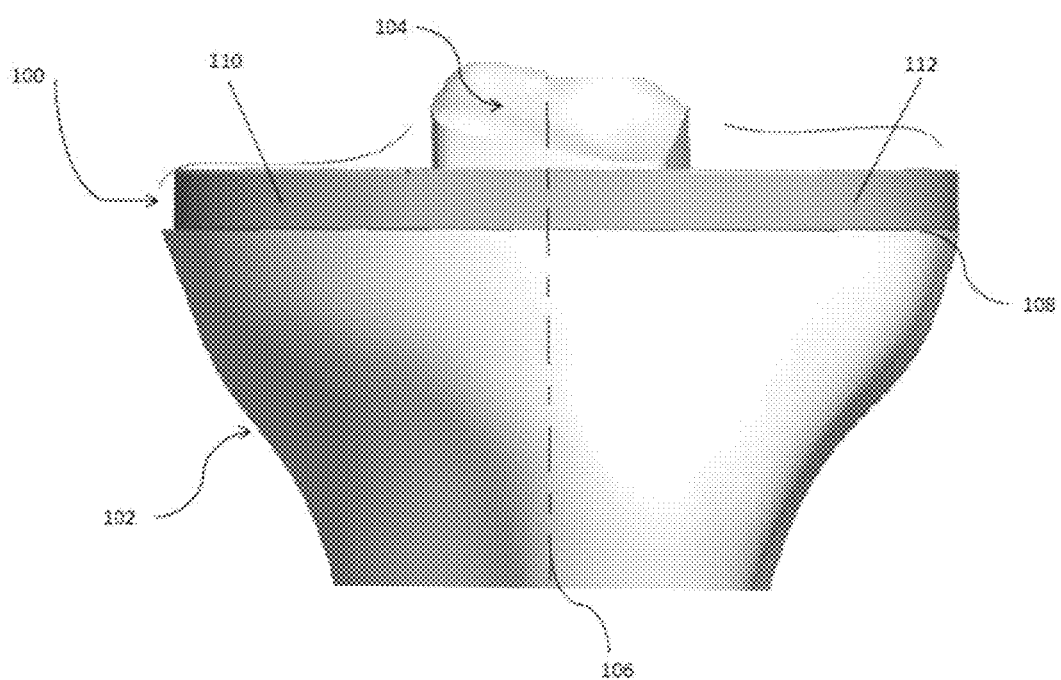
FIG. 1 is a front view of a prior art tibial baseplate engaged to a resected proximal tibia.

Referring to the drawings, wherein like reference numerals represent like elements, there is shown in the figures, in accordance with embodiments of the present invention, prosthetic implants, components or devices engaged to resected bone. FIG. 1 shows one embodiment of a prosthetic device, namely a tibial baseplate 100 used for restoring a patient's tibial mechanical alignment following a knee arthroplasty procedure. Tibial baseplate 100 has a proximal surface 101 and a distal surface 103 with a generally linear configuration. Distal surface 103 is configured to correspond to a resected surface 108 of a bone 102, which in this embodiment is the proximal tibia. Bone 102 may have certain anatomic features such as portions of the intercondylar eminence 104, for example, that the baseplate 100 is shaped to account for. The bone further has a mechanical axis 106, defined in this embodiment, as the line between a center of the knee joint and/or medial tibial spine and a center of the ankle joint (not shown).

Resected surface 108 forms an interface between tibial baseplate 100 and bone 102. In this embodiment, resected surface 108 is a planar resection having a slope in the coronal plane, such that a plane of the resected surface 108 is oblique or otherwise not perpendicular to mechanical axis 106. Tibial baseplate 100 has a corresponding linearly sloped orientation in the coronal plane, such that a medial portion 110 and a lateral portion 112 of tibial baseplate 100 are parallel and continuous.

In this embodiment, the slope of the resected surface 108 is in the direction of the patient's natural varus/valgus alignment, thus helping to restore the patient's natural varus/valgus orientation. However, one problem that has been recognized is that such an approach to mechanical realignment may also lead to baseplate loading that is off axial, providing a mechanical disadvantage at the bone/baseplate interface by introducing shear loads.

Figure 2:
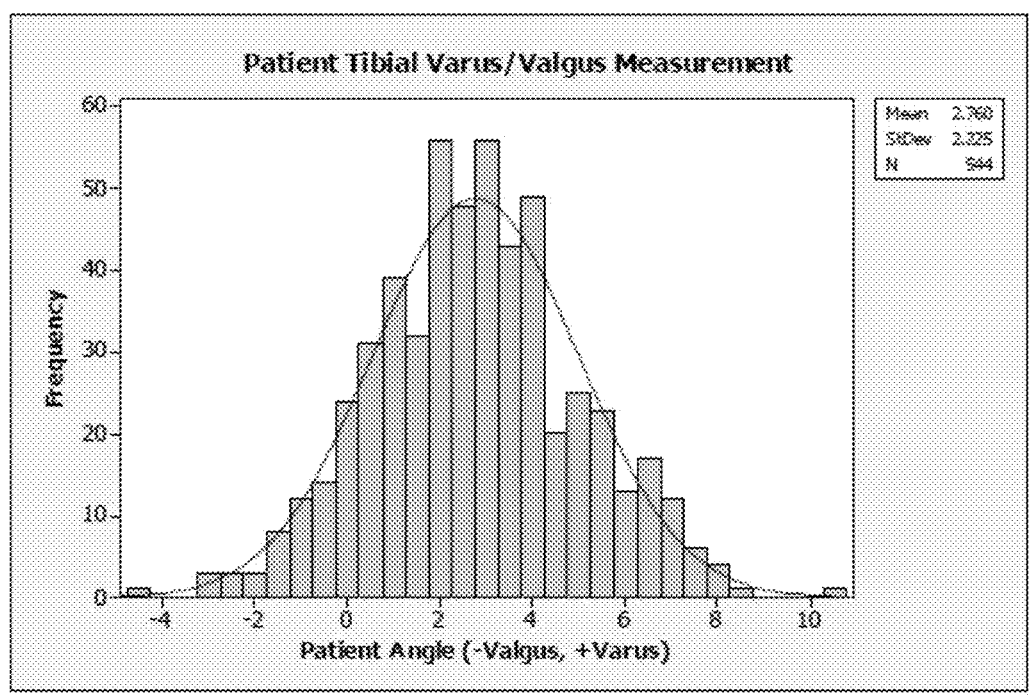
FIG. 2 is a histogram plotting measured values for the varus/valgus angle of patients and the corresponding number of those patients that have a certain varus/valgus angle.
Figure 3:
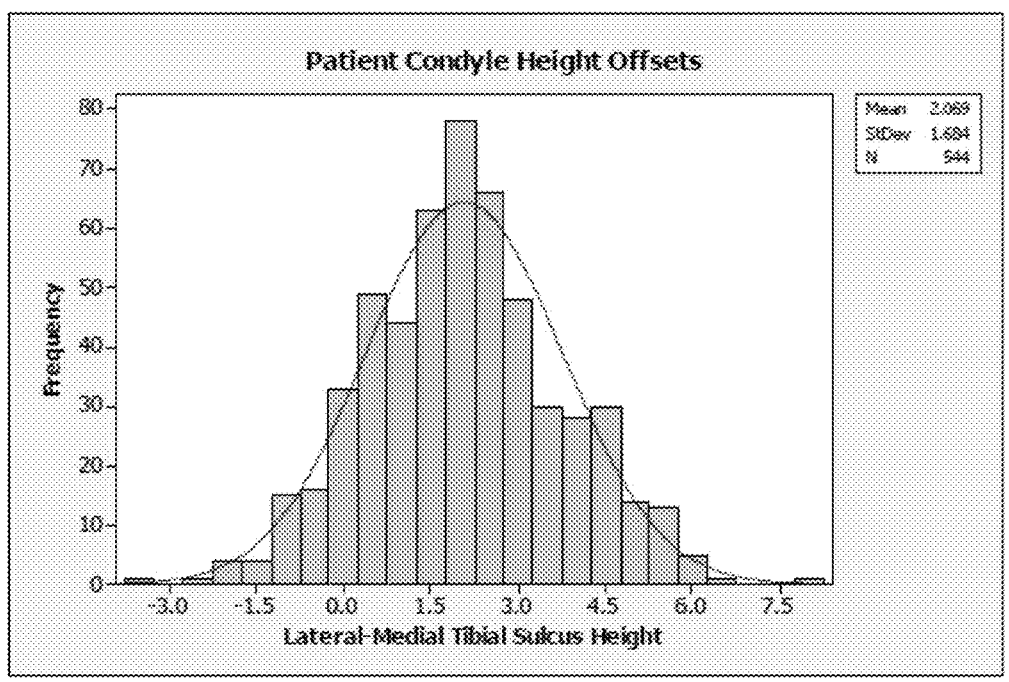
FIG. 3 is a histogram plotting measured values for the lateral-medial tibial sulcus height of patients and the corresponding number of those patients that have a certain lateral-medial tibial sulcus height.

FIGS. 2-3 present the results of an analysis of 544 patient tibiae, establishing that tibiae have on average a 2.76 degree of natural tibial varus and thus have a lateral condyle that is superior to the medial condyle relative to the tibial mechanical axis. Healthy patients tend to have a similar degree of joint and tibial varus. More extreme joint deviations from the tibial mechanical axis occur in osteoporotic patients, which on average tend to be in tibial varus. Surgical preparation based on the tibial mechanical axis tends to resect relatively more bone on the lateral tibia and requires an equivalent over resection on the medial femur. Further, surgical preparation based on anatomic alignment, on average, places implants in 2-3 degrees tibial varus resulting in off axis loading.

The following table presents the results of an analysis of 500 patients, in which 37 patients have an average of −1.48 degree of natural tibial valgus and thus have a medial condyle that is superior to the lateral condyle relative to the tibial mechanical axis.

| Patient Population | Average Angle | Number of Patients | Percent Population |
| --- | --- | --- | --- |
| Valgus (>0.5 degree) | −1.48427 | 37 | 6.8% |
| Varus (>0.5 degrees) | 3.356852 | 463 | 85.1% |

Figure 4:
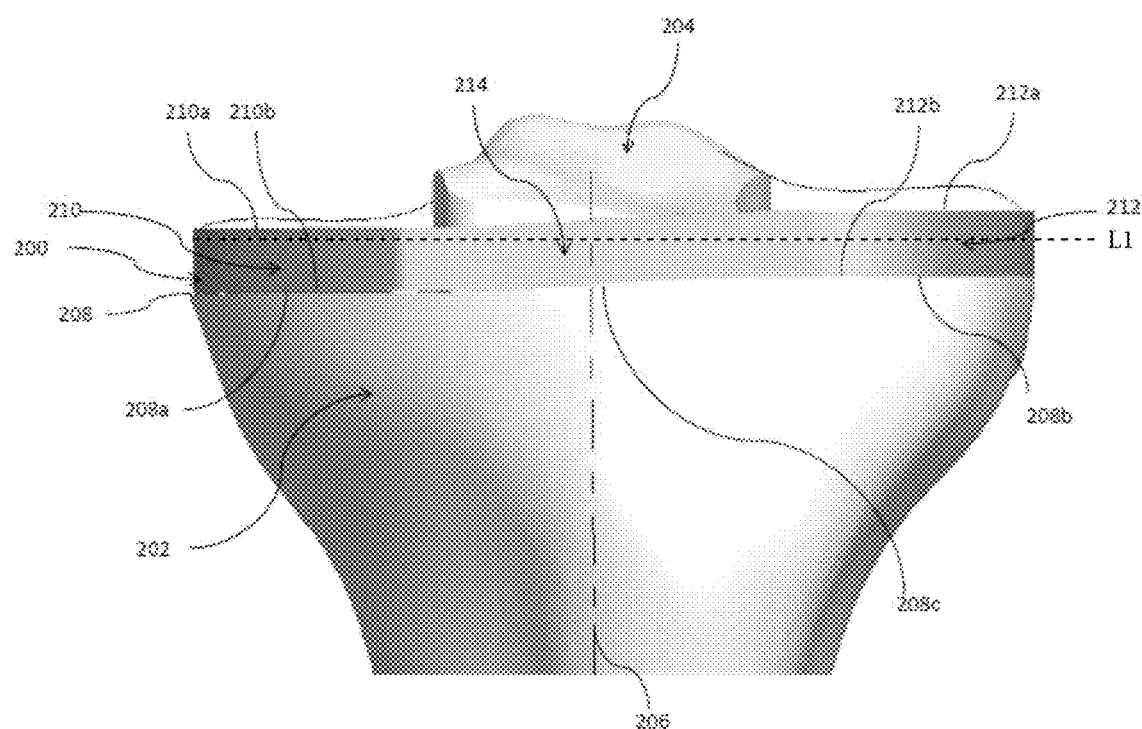
FIG. 4 is front plan view of one embodiment of a stepped tibial baseplate engaged to a resected proximal tibia.

FIG. 4 shows a front view of one embodiment of a stepped tibial baseplate useful in restoring mechanical alignment. A stepped tibial baseplate 200 abuts resected bone 202 of a proximal tibia. In this embodiment, bone 202 has retained certain proximal surface features that at least partially extend proximally beyond baseplate 200, including intercondylar eminence 204. Bone 202 has defined along its length a mechanical axis 206, which runs between the center of the knee joint or medial tibial spine and the center of the ankle joint (not shown).

Bone 202 has a resected surface 208 having both medial 208a and lateral 208b portions, corresponding respectively to the lateral and medial tibial condyles. The resected surface further has a stepped portion 208c between the medial 208a and lateral 208b portions as to create a vertical offset between the medial 208a and lateral 208b portions about mechanical axis 206. The medial 208a, lateral 208b, and stepped 208c portions are continuous as to create a continuous resection 208 across the surface of the bone 202. The medial 208a and lateral 208b portions are substantially parallel to one another about mechanical axis 206, but vertically offset from one another such that less bone is resected from the lateral tibia than what would be resected with a flat cut. In other words, medial portion 208a is therefore located inferiorly to proximal portion 208b about mechanical axis 206.

Similarly, baseplate 200 has medial 210 and lateral 212 portions corresponding to the medial 208a and lateral 208b resected surfaces of bone 202. The tibial baseplate 200 is further comprised of sets of opposing surfaces, such that the medial portion 210 has a proximal surface 210a and a distal surface 210b that is opposite proximal surface 210a. The lateral portion 212 has a proximal surface 212a and a distal surface 212b that is opposite proximal surface 212a. Tibial baseplate 200 includes a longitudinal axis L1 at least substantially parallel with proximal surfaces 210a, 212a and distal surfaces 210b, 212b. Proximal surface 210a lies along a plane P1 and proximal surface 212a lies along a plane P2, the planes P1 and P2 being parallel and offset to one another about longitudinal axis L1 of tibial baseplate 200. The tibial baseplate 200 further has an intermediate or stepped portion 214 coupling medial 210 and lateral 212 portions. The intermediate portion 214 has a proximal surface 214a and a distal surface 214b that is opposite proximal surface 214a. Proximal surface 214a is angled with respect to the proximal surfaces 210a, 212b of the medial 210 and lateral 212 portions. A first transition region 211 lies between the medial portion 210 and intermediate portion 214 and a second transition region 213 lies between intermediate portion 214 and lateral portion 212, the first transition region 211 forming a first radius and the second transition region 213 forming a second radius. The linear or lengthwise slope of medial 210 and lateral 212 portions is substantially perpendicular to mechanical axis 206 when viewed in the coronal plane. The linear or lengthwise slope of stepped portion 214 is oblique to mechanical axis 206, such as to produce a vertical offset between the medial 210 and lateral 212 portions in the coronal plane. Therefore, lateral portion 212 of the tibial baseplate 200 corresponding to lateral tibia resected surface 208b is located superiorly to medial portion 210 of tibial baseplate 200 corresponding to medial tibia resected surface 208a about mechanical axis 206.

Figure 5:
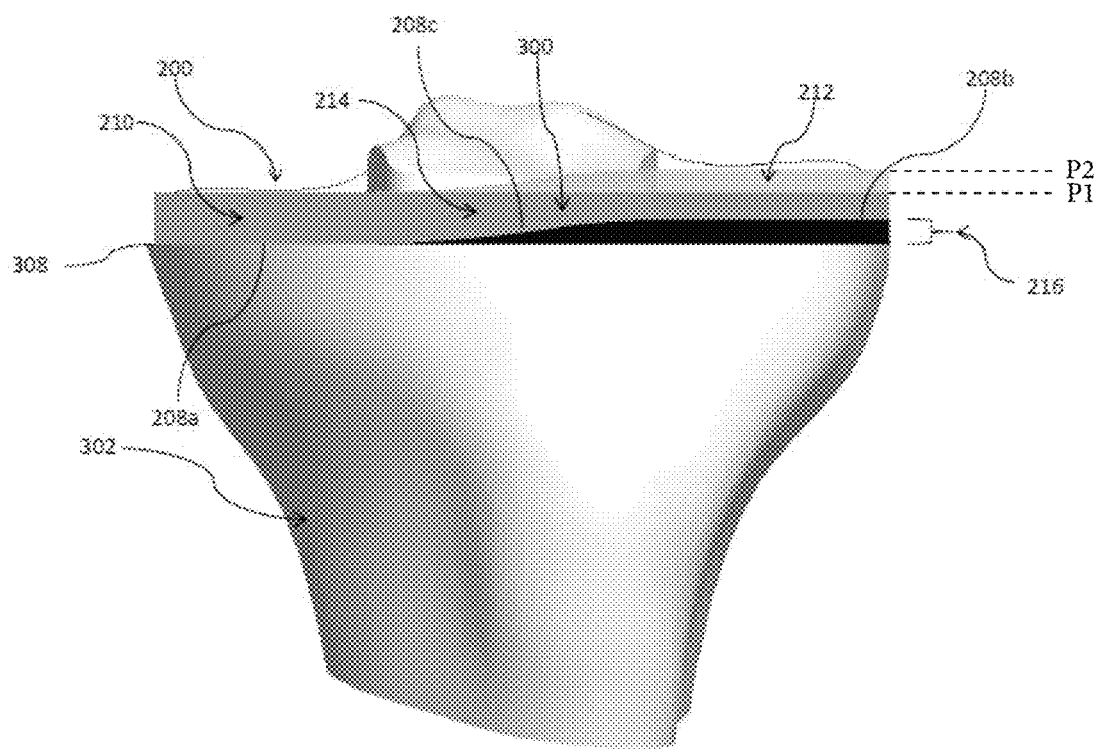
FIG. 5 shows a comparison between the stepped tibial baseplate of FIG. 4 and the tibial baseplate of FIG. 1.
Figure 6:
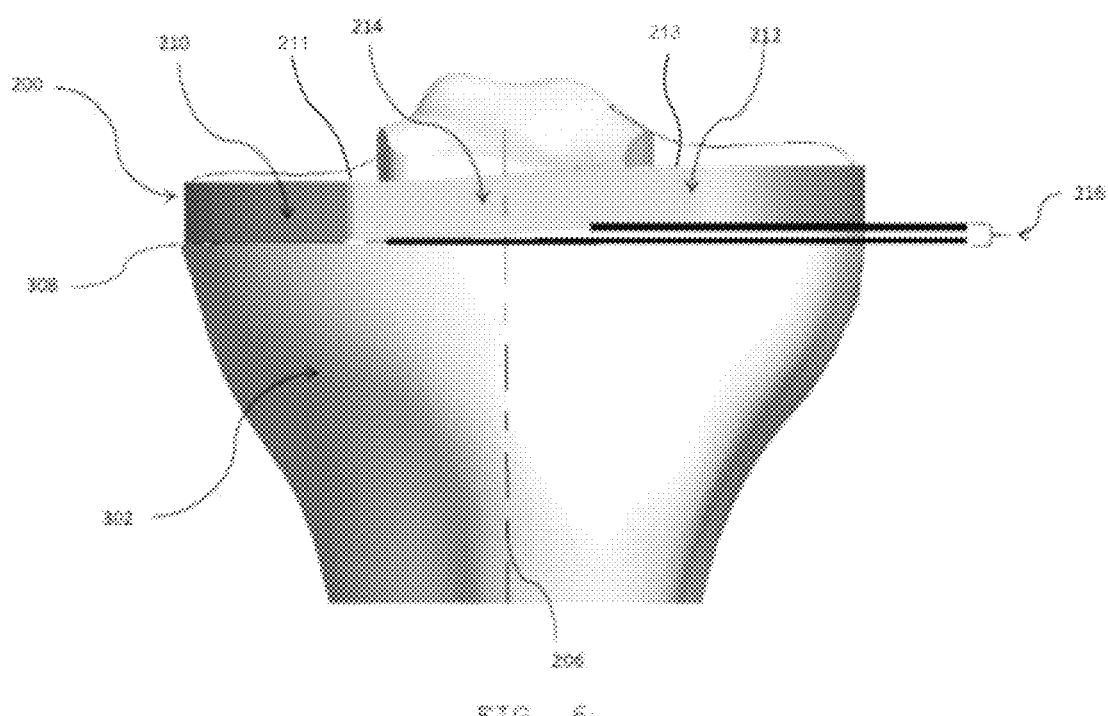
FIG. 6 shows a height difference between a plane of a first distal surface and a plane of a second distal surface of the stepped tibial baseplate of FIG. 4.

FIGS. 5-6 present additional views of aspects of stepped baseplate 200, illustrating a vertical offset 216 between the medial 210 and lateral 212 portions thereof. In FIG. 5, a perspective view is shown of stepped tibial baseplate 200 superimposed on a non-stepped or flat tibial baseplate 100 as shown in FIG. 1. Stepped baseplate 200 exhibits has a vertical offset 216 between medial portion 210 and lateral portion 212 thereof corresponding to the slope of the stepped portion 214. In contrast, tibial baseplate 100 without a stepped portion corresponds to a flat or planar resection 108 of bone 102 perpendicular to the mechanical axis of bone 102 when viewed in the coronal plane. The stepped tibial baseplate 200 therefore eliminates the need to resect the additional bone corresponding to the vertical offset 216 between the medial 210 and lateral 212 portions and therefore improves anatomic orientation and aids in preserving bone.

FIGS. 5-6 present additional views of aspects of stepped baseplate 200, illustrating a vertical offset 216 between the medial 210 and lateral 212 portions thereof. In FIG. 5, a perspective view is shown of stepped tibial baseplate 200 superimposed on a non-stepped or flat tibial baseplate 100 as shown in FIG. 1. Stepped baseplate 200 exhibits has a vertical offset 216 between medial portion 210 and lateral portion 212 thereof corresponding to the slope of the stepped portion 214. In contrast, tibial baseplate 100 without a stepped portion corresponds to a flat or planar resection 108 of bone 102 perpendicular to the mechanical axis of bone 102 when viewed in the coronal plane. The stepped tibial baseplate 200 therefore eliminates the need to resect the additional bone corresponding to the vertical offset 216 between the medial 210 and lateral 212 portions and therefore improve anatomic orientation and aid in preserving bone.

Figure 7:
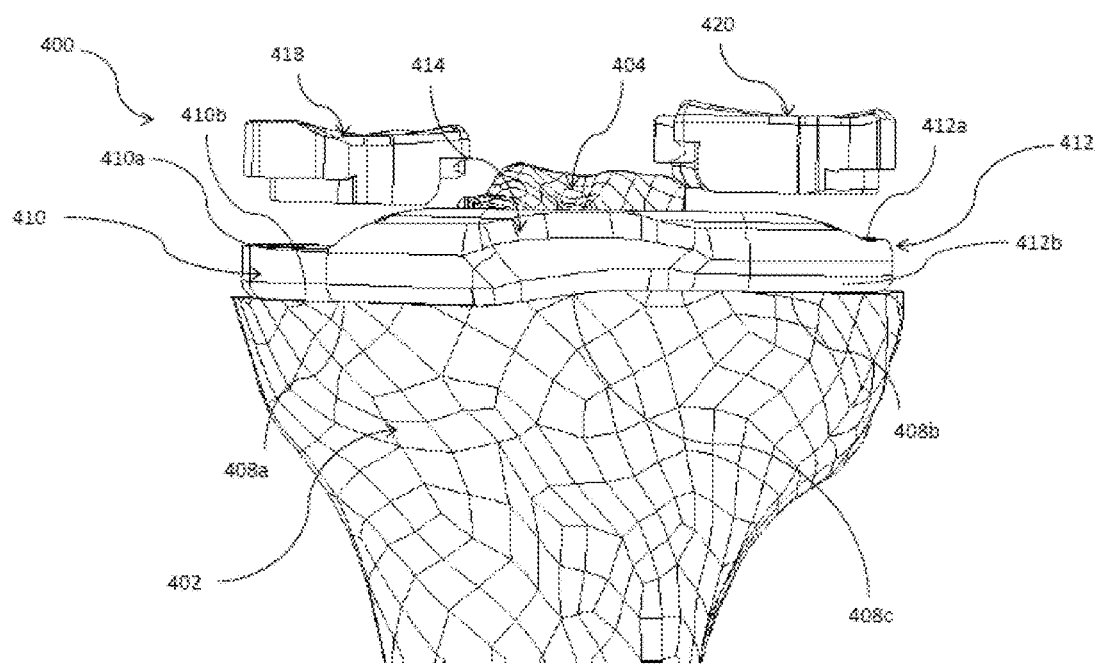
FIG. 7 is an exploded perspective view of one embodiment of a tibial implant system including a stepped tibial baseplate and corresponding medial and lateral inserts.
Figure 8:
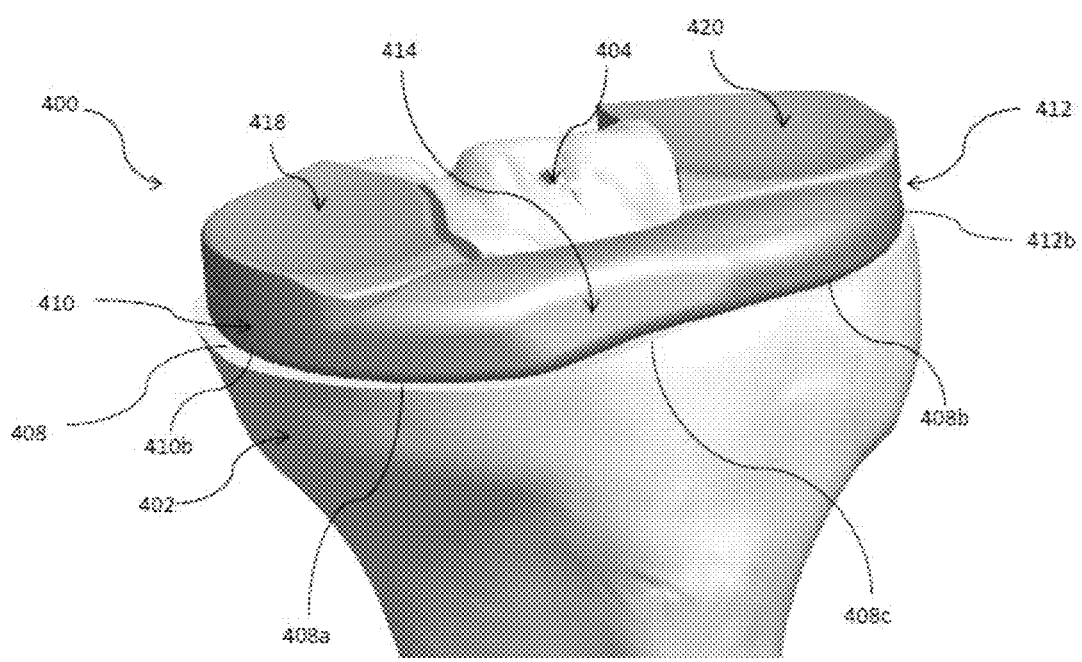
FIG. 8 is an assembled perspective view of the tibial implant system of FIG. 7.
Figure 9:
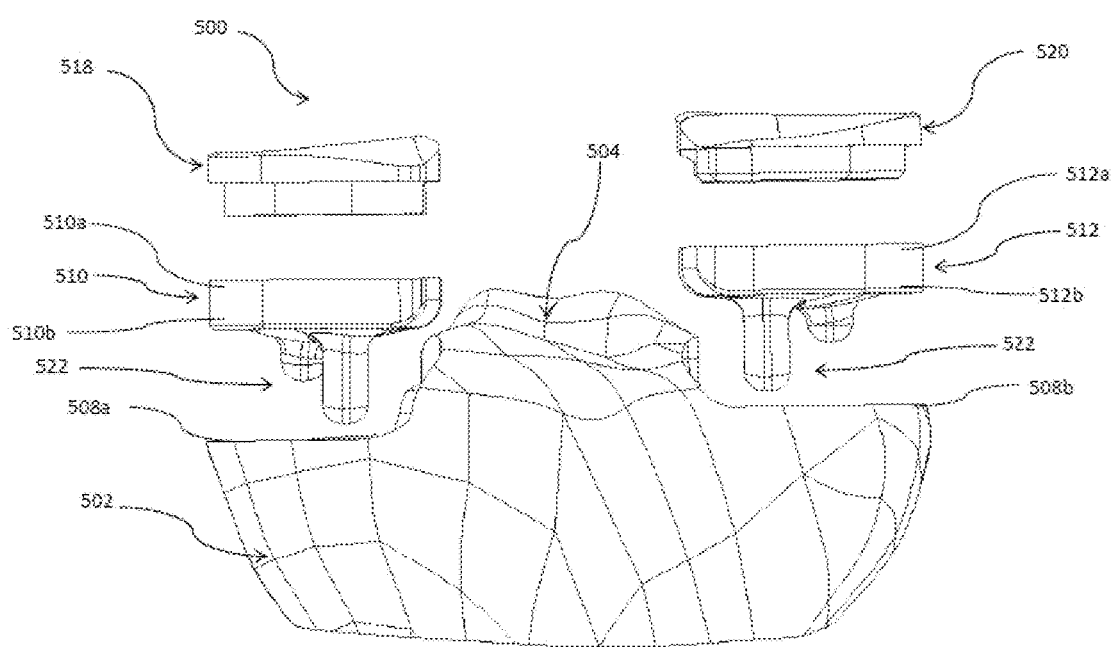
FIG. 9 is an exploded perspective view of one embodiment of a tibial implant system having medial and lateral unicondylar baseplates and corresponding medial and lateral inserts.
Figure 10:
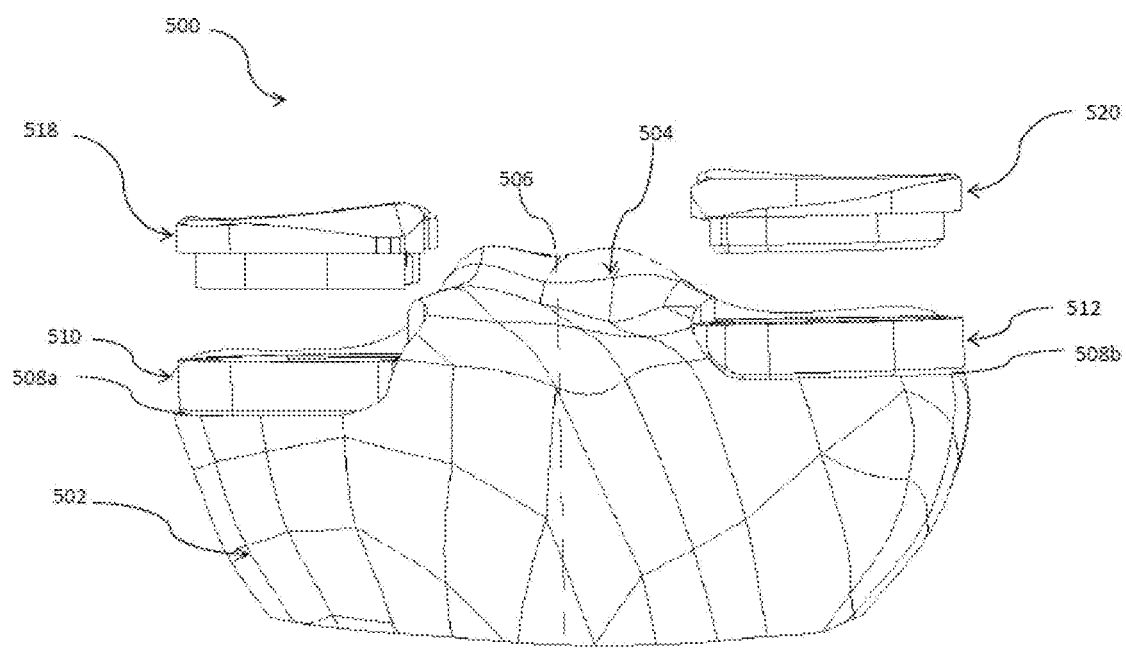
FIG. 10 is a partially assembled view of the tibial implant system of FIG. 9 showing the medial and lateral unicondylar baseplates engaged to resected portions of a proximal tibia.
Figure 11:
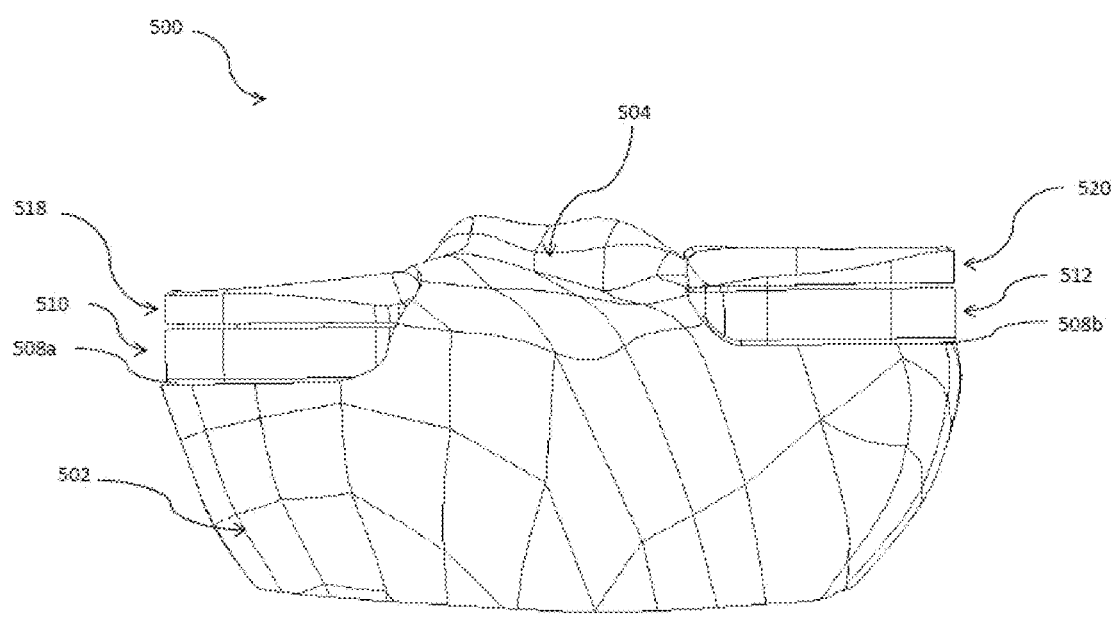
FIG. 11 is a front assembled view of the tibial implant system of FIG. 9.
Figure 12:
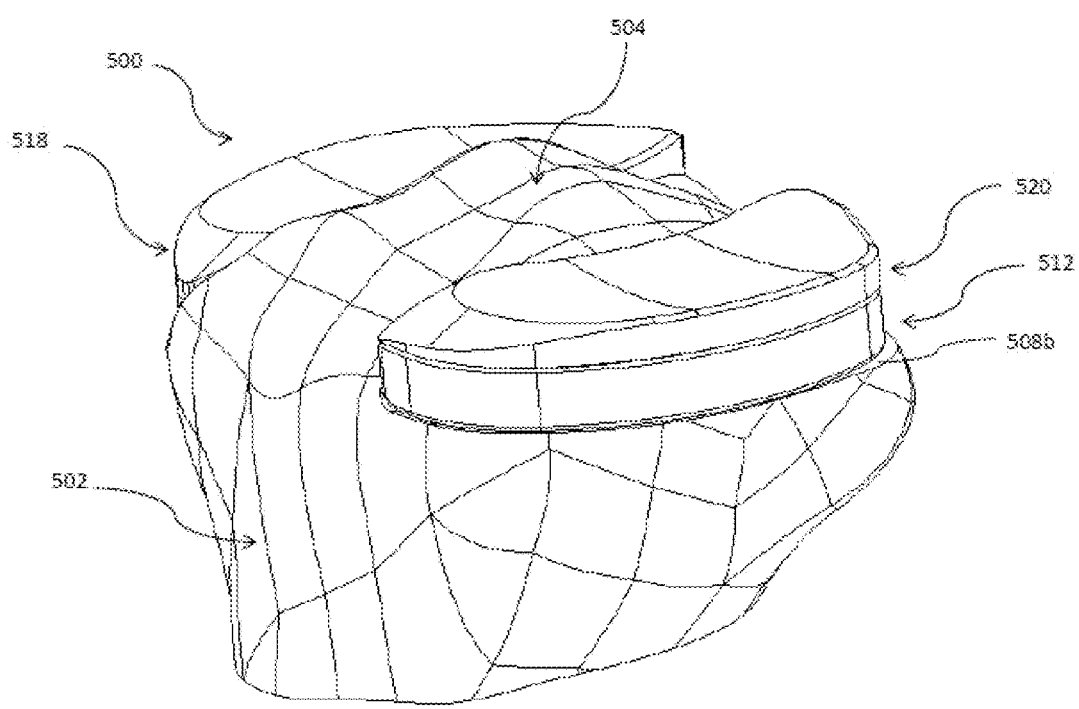
FIG. 12 is a perspective view of the tibial implant system of FIG. 9.
Figure 13:
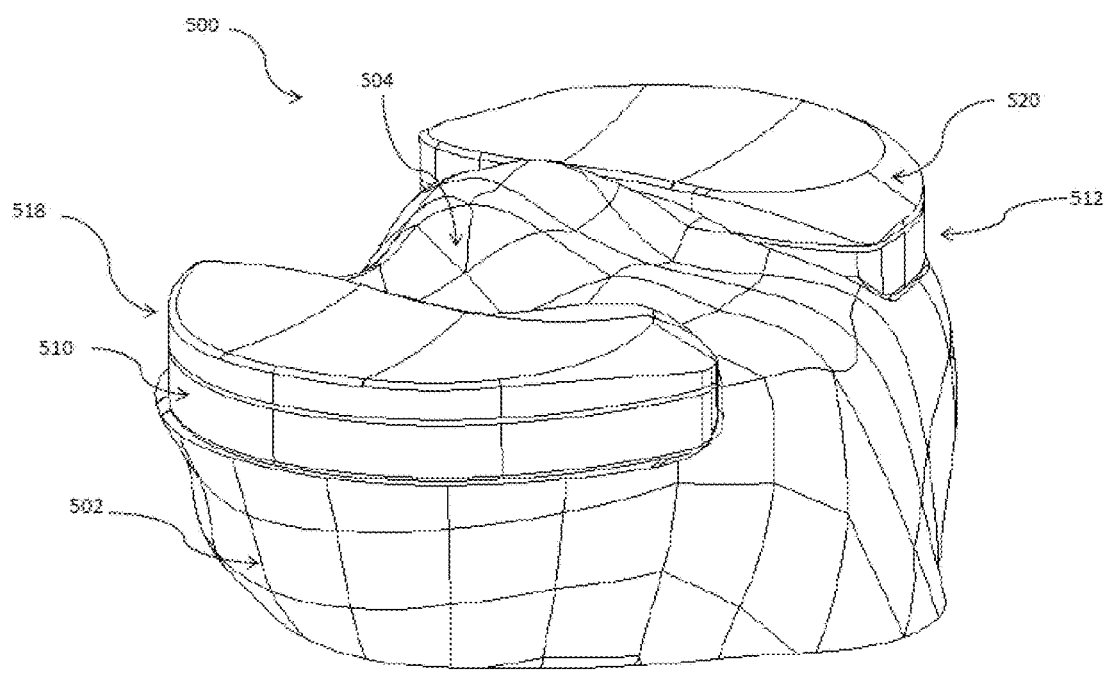
FIG. 13 is an alternate perspective view of the tibial implant system of FIG. 9.

FIGS. 7-8 present perspective views of a tibial implant system including a stepped tibial baseplate 400 and corresponding tibial inserts 418 and 420. In accordance with one aspect of this system, stepped baseplate 400 abuts a resected surface of bone 402, which in this example is a proximal surface of a tibia. The interface between the stepped tibial baseplate 400 and bone 402 is a resected bone surface 408. The resected surface has multiple portions or distinct stages when viewed in the coronal plane, including a medial portion 408a, a lateral portion 408b and a stepped portion 408c. The stepped tibial baseplate 400 has corresponding portions, including a medial portion 410, a lateral portion 412, and a stepped portion 414. Furthermore, the stepped tibial baseplate has opposite facing surfaces, such that the medial portion 410 has a first proximal surface 410a and a first distal surface 410b, such that the first distal surface is oriented opposite to the first proximal surface. Further, the lateral portion 412 has a second proximal surface 412a and a second distal surface 412b, such that the second distal surface is oriented opposite to the second proximal surface.

The stepped portion 414 of the stepped tibial baseplate 400 is bordered by medial 410 and lateral 412 portions. In the coronal view, the medial 410 and lateral 412 portions have longitudinal orientations that are parallel to a mechanical axis of bone 402. The stepped portion 414 has a longitudinal orientation that is sloped with respect to the mechanical axis, such that the medial portion 410 and the lateral portion 412 are vertically offset from one another about the mechanical axis with viewed in the coronal plane.

The medial 410 and lateral 412 portions of the stepped tibial baseplate 400 are configured to receive a medial insert 418 and a lateral insert 420, respectively. The first proximal surface 410a of the medial portion 410 is configured to receive medial insert 418, and the second proximal surface 412a of lateral portion 412 is configured to receive a lateral insert 420. The medial 418 and lateral 420 inserts may, for instance, be respectively configured to engage with lateral and medial femoral condyles. This may be achieved by configuring the medial 418 and/or lateral 420 inserts to have at least one concave articulating surface, for instance, in order to support a condyle or other bearing component.

The medial 410 and lateral 412 portions may also be configured such that the bone 402 retains certain surface features, including for example the intercondylar eminence 404. For example, the resected surface 408 of bone 402 may leave the eminence 404 either fully intact or partially intact. Where the eminence 404 is left fully or partially intact, the medial 410 and lateral 412 portions of the stepped tibial baseplate 400 may be configured around the structure of the eminence 404. One benefit of this configuration is that the stepped feature of the stepped tibial baseplate may reduce the amount of the eminence that is resected or otherwise replaced by the baseplate and/or insert.

The embodiments discussed herein have included monolithic tibial baseplate embodiments, wherein the tibial baseplate comprises a single piece or unitary structure, such that the medial and lateral portions are connected by a stepped portion. However, other aspects of the invention include a dual compartment, modular, stepped tibial baseplate having discrete medial and lateral portions.

FIGS. 9-13 show various views of a modular stepped tibial baseplate system having discrete medial and lateral baseplate portions. For instance, a modular stepped tibial baseplate 500 for repairing a bone 502 is shown, which in this example is a proximal tibia having a substantially retained intercondylar eminence 504. The surface of the bone 502 has a medial resected surface 508a and a lateral resected surface 508b corresponding to the location of the medial and lateral tibial condyles. In this example, the medial resected surface 508a includes a planar resection with an orientation that is perpendicular to a longitudinal axis 506 of the bone 502, which is the mechanical axis of bone 502 in this embodiment. Similarly, the lateral resected surface 508b includes a planar resection with an orientation that is perpendicular to a longitudinal axis 506 of bone 502.

The medial 508a and lateral 508b resected surface portions represent portions of the surface of the bone 502 that are resected in order to receive a corresponding medial 510 or lateral 512 baseplate portion. The medial baseplate portion 510 has a first proximal surface 510a and a first distal surface 510b. The lateral baseplate portion 512 has a second proximal surface 512a and a second distal surface 510b. The medial resected surface 508a forms an interface between the medial baseplate portion 510, and specifically the first distal surface 510b and bone 502. Similarly, the lateral resected surface 508b forms an interface between the lateral baseplate portion 512, and specifically the second distal surface 512b and the bone 502.

Tibial baseplate 500 does not require a stepped portion connecting the medial 510 and lateral 512 baseplate portions. Here, medial 510 and lateral 512 baseplate portions are modular or discrete, such that the medial 510 and lateral 512 baseplate portions are not connected or otherwise attached to each other. Rather, the medial resected surface 508a and the lateral resected surface 510b may be independently placed in a vertically offset orientation with respect to the longitudinal axis 506. Therefore, a stepped baseplate can be achieved with a medial resected surface 508a and a lateral resected surface 508b that have different positions along a longitudinal axis 506 of the bone 502.

In addition, the medial 510 and lateral 512 baseplate portions of the modular stepped tibial baseplate may be configured to receive a medial insert 518 and a lateral insert 520, respectively. The first proximal surface 510a of the medial portion 510 is configured to receive a medial insert 518, and the second proximal surface 512a of the lateral portion 512 is configured to receive a lateral insert 520. The medial 518 and lateral 520 inserts may, for instance, be respectively configured to engage with lateral and medial femoral condyles. This may be achieved by configuring the medial 518 and/or lateral 520 inserts to have at least one concave articulating surface, for instance in order to support a condyle or other bearing component.

Another feature of one embodiment includes fixation features 522 for attaching the medial 510 and lateral 512 baseplate portions to the bone 502. The fixation features 522 may include, for example, pegs or keels. Fixation features may also include those prepared so as to allow for a rotation about a single pivot point or different pivot points between the implant and the bone as described by U.S. Published Patent Application 2012/0330429, the entirety of which is hereby incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopaedic implant configured to replace an articular surface of a tibia comprising:
    medial, intermediate and lateral portions each having an articular surface and a bone contacting surface, the intermediate portion joining the medial and lateral portions,
    wherein the articular surfaces of the medial and lateral portions are concave and the articular surface of one of the lateral and medial portions is located superiorly to the articular surface of the other of the lateral and medial portions about a longitudinal axis of the orthopaedic implant and about a mechanical axis of the tibia when the orthopaedic implant is operatively engaged to the tibia, and
    wherein the articular surface of the intermediate portion is sloped with respect to the respective articular surfaces of the medial and lateral portions and from an inferior surface located adjacent to one of the lateral and medial portions to a superior surface located adjacent the other of the lateral and medical portion such that there is a smooth transition from the articular surface of the medial portion to the articular surface of the lateral portion,
    wherein the bone contacting surface of the medial and lateral portions each lie along a respective plane, the respective planes being parallel and offset to one another about the longitudinal axis of the orthopaedic implant.

2. The orthopaedic implant of claim 1, wherein the articular and bone contacting surfaces of the intermediate portion are parallel to one another.

3. The orthopaedic implant of claim 1, wherein the bone contacting surface of the intermediate portion is sloped with respect to the respective bone contacting surface of the medial and lateral portions.

4. The orthopaedic implant of claim 3, wherein the articular and bone contacting surfaces of the intermediate portion are sloped at different angles with respect to the respective articular surfaces of the medial and lateral portions.

5. The orthopaedic implant of claim 1, wherein the bone contacting surface of one of the lateral and medial portions is located superiorly to the bone contacting surface of the other of the lateral and medial portions about a longitudinal axis of the orthopaedic implant.

6. The orthopaedic implant of claim 1, wherein the bone contacting surfaces of the medial and lateral portions are coplanar.

7. The orthopaedic implant of claim 1, wherein the bone contacting surfaces of the medial, lateral and intermediate portions are coplanar.

8. The orthopaedic implant of claim 1, further comprising at least one engagement feature extending distally from at least one of the medial, proximal, or intermediate portions.

9. The orthopaedic implant of claim 1, further comprising a first transition region between the medial portion and the intermediate portion and a second transition region between the intermediate portion and the lateral portion, wherein the first transition region forms a first radius and the second transition region forms a second radius.

10. An orthopaedic implant configured to replace an articular surface of a tibia comprising:
    medial, intermediate and lateral portions each having an articular surface and a bone contacting surface, the intermediate portion joining the medial and lateral portions, the articular surfaces of the medial and lateral portions being concave,
    wherein the bone contacting surface of one of the lateral and medial portions is located superiorly to the articular surface of the other of the lateral and medial portions about a longitudinal axis of the orthopaedic implant and about a mechanical axis of the tibia when the orthopaedic implant is operatively engaged to the tibia, and
    wherein the bone contacting surface of the intermediate portion is sloped with respect to the respective bone contacting surfaces of the medial and lateral portions and from an inferior surface located adjacent to one of the lateral and medial portions to a superior surface located adjacent the other of the lateral and medical portion such that there is a smooth transition from the bone contacting surface of the medial portion to the bone contacting surface of the lateral portion,
    wherein the articular surface of the medial and lateral portions each lie along a respective plane, the respective planes being parallel and offset to one another about the longitudinal axis of the orthopaedic implant.

11. The orthopaedic implant of claim 10, wherein the articular and bone contacting surfaces of the intermediate portion are parallel to one another.

12. The orthopaedic implant of claim 10, wherein the articular surface of the intermediate portion is sloped with respect to the respective articular surfaces of the medial and lateral portions.

13. The orthopaedic implant of claim 10, wherein the articular surface of one of the lateral and medial portions is located superiorly to the articular surface of the other of the lateral and medial portions about a longitudinal axis of the orthopaedic implant.

14. The orthopaedic implant of claim 10, wherein the articular surfaces of the medial and lateral portions are coplanar.

15. The orthopaedic implant of claim 10, wherein the articular surfaces of the medial, lateral and intermediate portions are coplanar.

16. The orthopaedic implant of claim 10, further comprising at least one engagement feature extending distally from at least one of the medial, proximal, or intermediate portions.

17. The orthopaedic implant of claim 10, further comprising a first transition region between the medial portion and the intermediate portion and a second transition region between the intermediate portion and the lateral portion, wherein the first transition region forms a first radius and the second transition region forms a second radius.

18. A orthopaedic implant configured to replace an articular surface of a tibia comprising:
    medial, intermediate and lateral portions each having an articular surface and a bone contacting surface, the intermediate portion joining the medial and lateral portions,
    wherein the articular surfaces of the medial and lateral portions are concave and the articular surface of one of the lateral and medial portions is located superiorly to the articular surface of the other of the lateral and medial portions about a longitudinal axis of the orthopaedic implant and about a mechanical axis of the tibia when the orthopaedic implant is operatively engaged to the tibia, and wherein the articular and bone contacting surfaces of the intermediate portion are sloped with respect to the respective articular and bone contacting surfaces of the medial and lateral portions and from an inferior surface located adjacent to one of the lateral and medial portions to a superior surface located adjacent the other of the lateral and medical portion such that there is a smooth transition from the articular surface of the medial portion to the articular surface of the lateral portion and from the bone contacting surface of the medial portion to the bone contacting surface of the lateral portion wherein the bone contacting surface of the medial and lateral portions each lie along a respective plane, the respective planes being parallel and offset to one another about the longitudinal axis of the orthopaedic implant.

\* \* \* \* \*